United States Patent [19]

Melezoglu et al.

[11] 4,441,811
[45] Apr. 10, 1984

[54] APPARATUS AND METHOD FOR DETERMINING REFRACTIVE INDEX PROFILE IN A CYLINDRICAL ARTICLE

[75] Inventors: Cevdet Melezoglu, Corning; David J. Smith, Painted Post, both of N.Y.

[73] Assignee: Corning Glass Works, Corning, N.Y.

[21] Appl. No.: 300,796

[22] Filed: Sep. 10, 1981

[51] Int. Cl.³ ............................................. G01N 21/47
[52] U.S. Cl. ..................................... 356/128; 356/73.1
[58] Field of Search ........................ 356/73.1, 128, 129

[56] References Cited

U.S. PATENT DOCUMENTS 3,765,774 10/1973 Petrohilos ............................ 356/387
4,181,433 1/1980 Marcuse ............................... 356/128
4,227,806 10/1980 Watkins ............................... 356/73.1

OTHER PUBLICATIONS

Chu, P. L. "Nondestructive Measurement of Index Profile of an Optical-Fiber Preform," *Electronics Letters*, vol. 13, No. 24, (Nov. 24, 1977), pp. 736-738.

Marcuse, D. "Refractive Index Determination by the Focusing Method," *Applied Optics*, vol. 18, No. 1, (Jan. 1, 1979), pp. 9-13.

Chu, P. L. et al., "Measurement of Refractive Index Profile of Optical-Fiber Preform," *Electronics Letters*, vol. 15, No. 10, (May 10, 1979), pp. 295-296.

Watkins, L. S. "Laser Beam Refraction Traversely Through a Graded-Index Preform . . . ," *Applied Optics*, vol. 18, No. 13, (Jul. 1, 1979), pp. 2214-2222.

*Primary Examiner*—R. A. Rosenberger
*Attorney, Agent, or Firm*—K. van der Sterre; C. S. Janes, Jr.

[57] ABSTRACT

Apparatus and a method for analyzing the refractive index profile of a cylindrical, transparent optical waveguide preform, utilizing a scanning light beam to traverse a fixed preform and a refractor to direct light deflected by the preform onto a displacement sensor, is described.

2 Claims, 4 Drawing Figures

APPARATUS AND METHOD FOR DETERMINING REFRACTIVE INDEX PROFILE IN A CYLINDRICAL ARTICLE

BACKGROUND OF THE INVENTION

The present invention is in the field of optical waveguide manufacture and relates particularly to apparatus for analyzing the optical characteristics of transparent, cylindrically symmetric articles such as optical waveguide preforms.

Many of the processes presently used to fabricate glass optical waveguide fibers involve the preparation of a cylindrical glass preform which is inspected before it is drawn into the final waveguide filament. The refractive index distribution within this preform ordinarily dictates the refractive index distribution obtainable in the drawn filament, which in turn controls the propagation characteristics of the waveguide. The desirability of examining the preform to determine whether it will provide an appropriate refractive index profile in filament form has thus been recognized, and several techniques for determining this refractive index distribution have been proposed.

P. L. Chu, *Electronics Letters*, 13 (24), pp. 736–738 (1977), has noted that the refractive index profile of an optical waveguide preform can be deduced from the exit trajectories of a series of parallel light rays entering the preform at right angles to its axis and back-scattered therefrom. D. Marcuse, *Applied Optics*, 18 (1), pp. 9–13 (1979), has shown that the refractive index distribution in a fiber or preform can be determined by observing the power distribution in a light field behind a preform or fiber front-illuminated by a broad, collimated light beam. I. Sasaki et al., *Electronics Letters*, 16 (6), pp. 220–221 (1980), have described a technique wherein spatial filtering of the light traversing a front-illuminated preform yields a shadow image of the deflection function, but the technique relies on a traversing diode array. L. S. Watkins, *Applied Optics*, 18(13), pp. 2214–2222, describes a procedure for computing the profile coefficient α and the refractive index difference Δ between the center and outer core, but does not directly calculate the index as a function of preform radius.

The refractive index profile of an optical waveguide preform is commonly defined by a function correlating the refractive index of the preform at a given point with the radial distance of the point from the central axis of the preform. In *Applied Optics*, supra, Marcuse reports an expression for calculating the refractive index n(r) of a preform at radius r from the preform axis, based on the exit trajectories of parallel incoming light rays traversing the preform and refracted thereby, as follows:

$$n(r) - n_c = \frac{n_c}{\pi L} \int_r^a \frac{t - y(t)}{(t^2 - r^2)^{\frac{1}{2}}} dt \qquad (1)$$

wherein:
n(r) = the refractive index of the preform at radius r
$n_c$ = the refractive index of the outer layer of the preform
t = the entrance height of an incoming ray
a = the radius of the preform
L = the distance from the preform to an observation plane located behind the preform
y(t) = the height, in the observation plane, of the exiting refracted ray having incoming height t The height of the entering ray and the height of the refracted ray at the observation plane refer to the spacings of these rays from an optical axis parallel to the incoming rays and intercepting the axis of the waveguide preform.

In the Marcuse method, t and y(t) are not obtained directly but must be calculated from the power distribution of refracted light at the observation plane by an integration, with n(r) then being calculated by a second integration. This approach somewhat reduces the sensitivity of the method to fine detail in the refractive index profile of the optical waveguide preform.

SUMMARY OF THE INVENTION

In accordance with the present invention, problems with the power distribution method are avoided and the measurement apparatus considerably simplified by directly determining the index profile n(r) from measurements in an apparatus utilizing a scanning light beam to traverse a fixed preform. A narrow beam of light from a suitable fixed source strikes a rotatable reflector causing the beam to scan a convergent refractor. The convergent refractor directs the light along paths in a scanning plane in directions parallel to the optical axis of the apparatus so that the light intercepts the optical waveguide preform to be examined.

The preform, immersed in an index-matching fluid, is perpendicular to the scanning plane and the light traversing the preform, while remaining in the scanning plane, is angularly deflected from its incoming direction. This deflected light traverses a second refractor which directs the light to a sensor positioned on the scanning plane in the focal plane of the second refractor.

Any light which is not deflected by the preform, e.g., light traversing the preform axis or light missing the preform entirely, is caused by the second refractor to strike the sensor on the optical axis of the apparatus. Any light which is deflected by the preform is caused by the second refractor to strike the sensor at a point which is displaced away from the optical axis. The sensor records the extent of this displacement for various incoming ray heights t, and the refractive index of the preform at a given radius is then directly computed from the displacements by a single numerical integration as hereinafter set forth.

Utilizing the method and apparatus of the present invention the refractive index profile of essentially any transparent optical waveguide preform, whether for step-index, graded-index, or single-mode waveguide fiber, can readily be ascertained. Further, the invention extends to the analysis of essentially any glass, plastic, or other transparent cylindrical article having any form which appropriates a solid of rotation about an axis of symmetry where information about the refractive index distribution in the article is desired.

BRIEF DESCRIPTION OF THE DRAWINGS

The invention may be further understood by reference to the drawings wherein.

DETAILED DESCRIPTION

Figure 1:
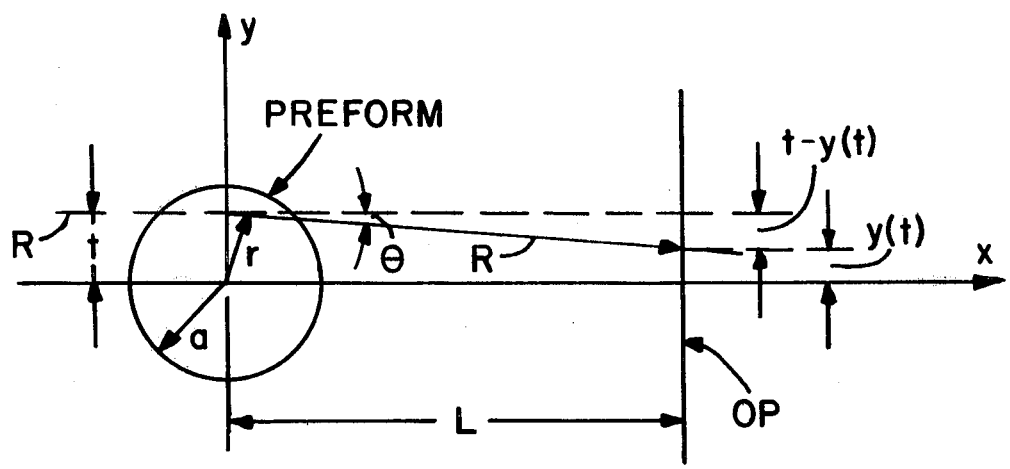
FIG. 1 schematically illustrates the deflection of a beam of light by a transparent optical waveguide preform.

FIG. 1 of the drawing schematically shows, in cross section, an optical waveguide preform traversed by a light ray R showing the parameters t, y(t) and L which are used to calculate the refractive index profile of the preform in accordance with equation (1) above. As already noted, the variables which must be determined for the computation are t, the entrance height of a light ray R which is the spacing of the ray from the x-axis, and y(t), the height of the ray in observation plane OP spaced a distance L from the preform, which is used to calculate the values of $t-y(t)$ to be used in the integration.

Figure 2:
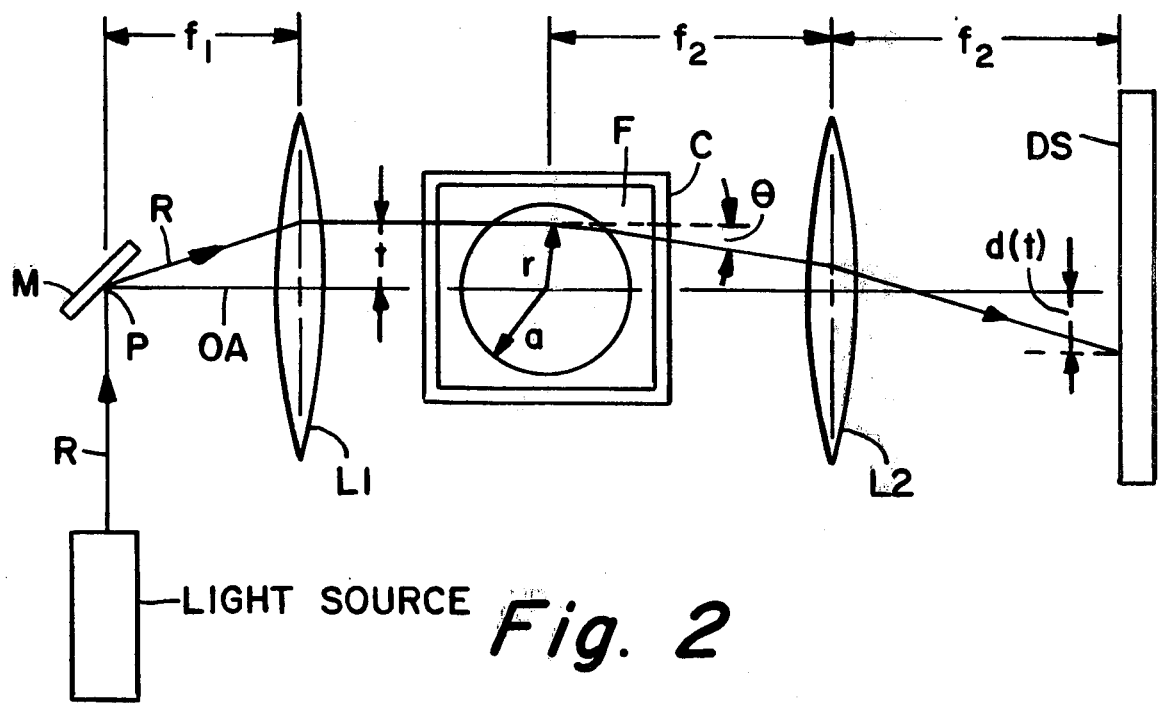
FIG. 2 schematically illustrates apparatus suitable for evaluating an optical waveguide preform in accordance with the invention.

Referring to FIG. 2 of the drawing, apparatus in accordance with the present invention comprises a fixed light source for generating and propagating a narrow collimated beam of light R along a path toward a scanning mirror M. This scanning mirror constitutes rotatable reflecting means positioned at an interception point P on the light path for reflecting the light R from the interception point over a range of selected angles in a scanning plane, which in the present case corresponds to the plane of the drawing.

An optical waveguide preform clamped in a suitable support is partially immersed in index matching fluid F in a transparent chamber C constituting a fixed work station in the scanning plane such that the preform intersects the scanning plane at right angles thereto. Positioned between the work station and rotatable reflecting means M is a first convergent refracting means L1, such as a spherical lens, having a focal length $f_1$ and being spaced a distance $f_1$ from the point of interception P of light beam R on the rotatable reflector. This refracting means operates to refract light reflected from the interception point and to direct that light along paths toward the preform in the scanning plane and parallel to the optical axis OA of the apparatus. The optical axis OA of the apparatus is the extension of a line joining interception point P on the rotatable reflection means M and the diametric center of the cross-section of the preform in the scanning plane at the work station. This center is a point on the axis of the cylindrical preform.

After the light has traversed the preform and has been deflected through an angle, e.g., angle $\theta$, it traverses a second convergent refracting means L2 having a focal length $f_2$ which is also positioned on the optical axis. This refractor intercepts and refracts light traversing the preform, whether or not angularly deflected by refraction therein, and directs it to displacement sensing means DS in the scanning plane and spaced a distance $f_2$ from the second refractor. The displacement sensor DS intercepts the light refracted by the second refractor and senses the positional displacement d(t) thereof away from the optical axis, as a result of angular deflection $\theta$ caused by passage through the preform.

The method for using the displacement d(t) to compute the refractive index of the preform at a radius r from the preform axis can be understood by reference to FIGS. 1 and 2 of the drawing. From FIG. 1, we can write $$\tan \theta = \frac{t - y(t)}{L} \quad (2)$$

As indicated in FIG. 2, the displacement sensor in the apparatus of the present invention is located at a distance $f_2$ from refractor L2, and is thus in the focal plane of the refractor. Therefore, one can write $$\tan \theta = \frac{d(t)}{f_2} \quad (3)$$

By combining equations (2) and (3) above, one can write $$t - y(t) = \frac{L \, d(t)}{f_2} \quad (4)$$

As seen from FIG. 2, the preform may be positioned such that the distance between the preform axis and the second refractor (the distance L in FIG. 1) is equal to $f_2$. In that case, equation (4) can be rewritten:

$$t - y(t) = d(t) \quad (5)$$

By substituting equation (5) into equation (1) above, one can write $$n(r) - n_c = \frac{n_c}{\pi f_2} \int_r^a \frac{d(t)}{(t^2 - r^2)^{\frac{1}{2}}} dt \quad (6)$$

In actuality, the value of d(t) for a given ray does not depend directly on the distance between the preform and L2, provided the deflected ray traverses L2. Thus, preform-to-L2 distance is not critical, although values of about $f_2$ or slightly more than $f_2$ have provided the best measurement sensitivity.

In order to calculate a value n(r) utilizing the apparatus of the invention, the entrance height t of each ray passing through the first refractor and entering the preform is correlated with the measured value of d(t) for that ray ascertained by means of the sensor behind the second reflector. The integration of equation (6) is then numerically evaluated for each value of r using the appropriate t and d(t) values and a refractive index profile as a function of radius r in the preform can then be plotted.

The invention may be further understood by reference to the following detailed example describing the examination of an optical waveguide preform in accordance therewith.

EXAMPLE

A transparent glass optical waveguide preform having a length of about 50 cm and a diameter of about 7.5 cm is selected for analysis. This preform comprises a solid core having a gradient index of refraction and a cladding of substantially uniform retractive index.

The preform is clamped into a work station comprising a transparent chamber filled with index matching fluid. The sides of the chamber to be traversed by the light beam are plane parallel plates perpendicular to the optical axis of the device. The preform clamping device is a rotatable chuck mounted on a lathe carriage which supports the preform so that it is perpendicular to the scanning plane. Although fixed for a particular measurement, the preform can thus be rotated about its axis and also translated along its axis between runs to move a selected cross-section of the preform into the scanning plane for analysis. The chamber is provided with a thermostatically controlled electric heater so that the temperature and thus the refractive index of the fluid can be maintained at a constant value, approximating that of the preform outer layer.

A light source consisting of a 5mW He-Ne laser with collimating optics, Model LSR5P HD from Aero Tech, Inc., Pittsburgh, PA, is activated and the output is passed to a rotatable mirror which in rotation scans the beam across a diameter of an achromatic double convex glass lens having a focal length of about 30 cm. The lens is positioned 30 cm from the point on the rotating mirror from which the reflected output of the light source originates.

The scanning mirror is rotated so that the reflected, refracted beam scans the cross section of the preform in the scanning plane from one edge of the circular cross section to the other. The deflected exiting beam is refracted by a second double convex glass lens having a focal length of 30 cm and spaced 30 cm from the preform axis and falls on a pin diode linear position sensor, model PIN-LSC/4 from United Detector Technology, Inc., Santa Monica, CA, positioned 30 cm from the second lens. The displacement of the beam on the sensor away from the optical axis of the apparatus is recorded, along with the position of the scanning mirror at the time each displacement recording is made.

Figure 3:
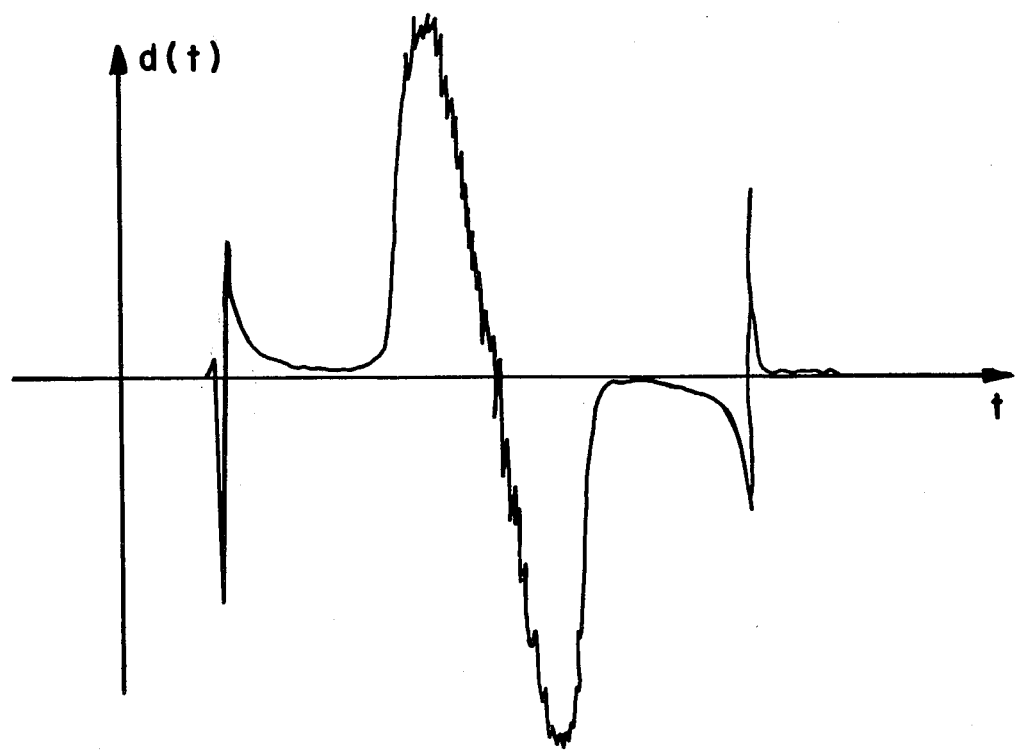
FIG. 3 plots data generated by apparatus such as illustrated in FIG. 2.

A plot of displacement value d(t) as a function of incoming ray height t computed from the mirror angle can be generated from the recorded data. Such a plot is shown in FIG. 3 of the drawing wherein relative ray entrance height t is shown on the horizontal axis and relative ray displacement d(t) is reported on the vertical axis. Up to 4000 pairs of t and d(t) values may be used to generate such a plot.

Computations of the refractive index of the preform at each of up to 4000 values of r can be numerically computed from the data plotted in FIG. 3 utilizing equation (6) above. These values can be shown on a plot of refractive index as a function of preform radius to give an accurate representation of the profile of the preform.

Figure 4:
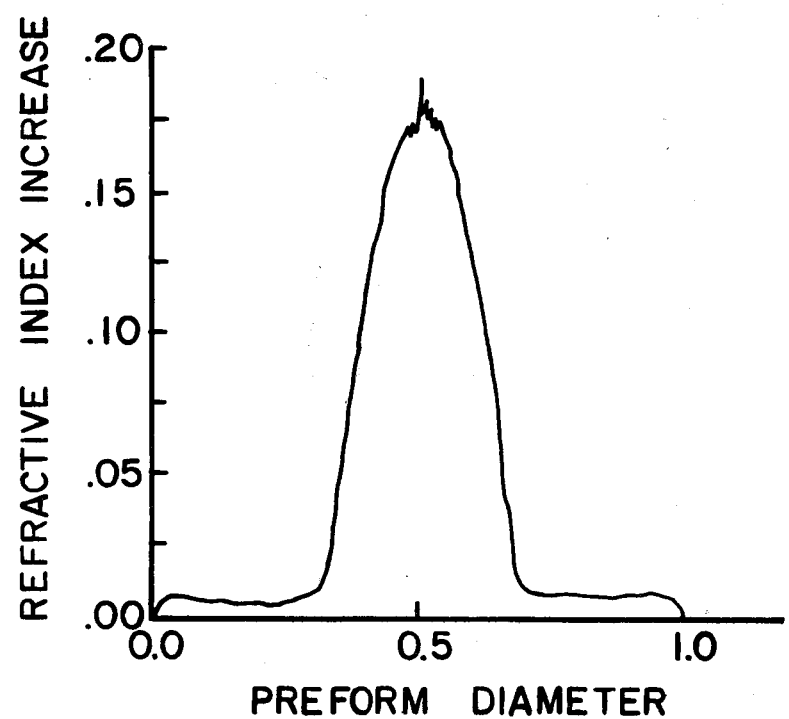
FIG. 4 is a plot of the refractive index profile of an optical waveguide preform evaluated from data such as shown in FIG. 3.

FIG. 4 of the drawing shows a profile numerically computed from the deflection data shown in FIG. 3 of the drawing. Position on the preform diameter is shown on the horizontal axis and change in refractive index is shown on the horizontal axis. The relatively flat refractive index characteristic of the cladding and the near-parabolic refractive index profile of the core are clearly apparent from the drawing. Other determinations which can be made using data such as shown in FIG. 4 are preform dimensions, preform eccentricity, core diameter, core:cladding ratio and the absolute refractive index values of the core and cladding, given the refractive index of the matching fluid.

Of course, the foregoing example is merely illustrative of methods and apparatus which could be employed in accordance with the invention. Obviously, many variations and modifications thereupon may be resorted to by those skilled in the art within the scope of the appended claims.

We claim:

1. In optical apparatus for analyzing the optical characteristics of a transparent, cylindrical, radially symmetric article comprising source means for generating a narrow collimated beam of light along a path, rotatable reflecting means positioned at an interception point on the path for reflecting light from the interception point over a range of selected angles in a scanning plane, support means for supporting the transparent cylindrical article in index-matching fluid at a fixed work station in the scanning plane such that the article intersects said plane at right angles thereto, first convergent refracting means L1 having focal length $f_1$ positioned between the reflecting means and the work station and on an optical axis joining the interception point and the cylinder axis of the article for directing light from the reflecting means through the cylindrical article, second convergent refracting means L2 of focal length $f_2$ positioned on the optical axis behind the article to refract the light traversing the article, and displacement sensor means on the optical axis behind refractor L2 for intercepting the light refracted thereby, the improvement characterized in that:

the second convergent refractor L2 of focal length $f_2$ is positioned a distance $f_2$ from the cylinder axis of the article, with the displacement sensor being positioned a distance $f_2$ from the second convergent refractor L2, such that a displacement value d(t) output by the sensor, corresponding to the displacement from the optical axis at the sensor of a narrow light beam reaching the sensor from the source, corresponds exactly to the ray displacement function (t-y(t)) from the integral expression:

$$n(r) - n_c = \frac{n_c}{\pi L} \int_r^a \frac{(t - y(t))}{(t^2 - r^2)^{\frac{1}{2}}} dt$$

for calculating the refractive index profile of a cylindrical article.

2. In the method of determining a refractive index value n(r) at radius r of a transparent, cylindrically symmetric article of outer radius a and outer refractive index $n_c$ wherein parallel light rays are directed through a planar cross-section of the article at entrance heights t corresponding to the distances of the rays from an optical axis parallel with the rays and intersecting the cylinder axis of the article, and the points of intersection y(t) of the rays exiting the cylinder with an observation plane spaced a distance L from the cylinder axis are ascertained and used to calculate the value of n(r) from the integral expression:

$$n(r) - n_c = \frac{n_c}{\pi L} \int_r^a \frac{(t - y(t))}{(t^2 - r^2)^{\frac{1}{2}}} dt$$

the improvement wherein a convergent refractor L2 of focal length $f_2$ is positioned on the optical axis at a distance $f_2$ from the cylinder axis of the article to intercept a narrow collimated light beam traversing the cylinder from the source, said refractor then directing the beam onto a displacement sensor positioned a distance $f_2$ from refractory L2 such that the value of the displacement d(t) of the beam from the optical axis at the displacement sensor corresponds to and can be substituted for the value (t−y(t)) in the said integral expression.

* * * * *